United States Patent
Pratt et al.

(10) Patent No.: US 11,740,216 B2
(45) Date of Patent: *Aug. 29, 2023

(54) METHOD AND APPARATUS FOR MEASURING HUMIDITY USING AN ELECTROCHEMICAL GAS SENSOR

(71) Applicant: Honeywell International Inc., Charlotte, NC (US)

(72) Inventors: Keith Pratt, Portsmouth (GB); Tom Gurd, Eastleigh (GB)

(73) Assignee: HONEYWELL INTERNATIONAL INC., Charlotte, NC (US)

( * ) Notice: Subject to any disclaimer, the term of this patent is extended or adjusted under 35 U.S.C. 154(b) by 87 days.

This patent is subject to a terminal disclaimer.

(21) Appl. No.: 17/316,142

(22) Filed: May 10, 2021

(65) Prior Publication Data

US 2021/0262998 A1 Aug. 26, 2021

Related U.S. Application Data

(63) Continuation of application No. 16/376,624, filed on Apr. 5, 2019, now Pat. No. 11,029,294.

(51) Int. Cl.
*G01N 27/404* (2006.01)
*G01N 33/00* (2006.01)
(Continued)

(52) U.S. Cl.
CPC ........... *G01N 33/0031* (2013.01); *G01K 1/14* (2013.01); *G01N 27/4045* (2013.01); *G01N 27/413* (2013.01); *G01N 33/0036* (2013.01)

(58) Field of Classification Search
CPC ........... G01N 33/0031; G01N 27/4045; G01N 27/413; G01N 33/016; G01K 1/14
See application file for complete search history.

(56) References Cited

U.S. PATENT DOCUMENTS

| 9,213,016 | B1 | 12/2015 | Stetter et al. |
| 11,029,294 | B2 * | 6/2021 | Pratt ............... G01N 27/413 |
| 2019/0018067 | A1 | 1/2019 | Kong et al. |

FOREIGN PATENT DOCUMENTS

| CN | 207424661 U | * | 5/2018 | ........... G05B 19/418 |
| JP | 2017-062195 A | | 3/2017 | |

(Continued)

OTHER PUBLICATIONS

EPO computer-generated English language translation of Chen et al. CN 207424661 U, patenet published May 29, 2018 (Year: 2018).*

(Continued)

*Primary Examiner* — Alexander S Noguerola
(74) *Attorney, Agent, or Firm* — Alston & Bird LLP

(57) ABSTRACT

A gas detection apparatus and method for measuring humidity using an electrochemical gas sensor. The gas detection apparatus comprises an electrolyte-based electrochemical gas sensor and a controller configured to measure the average humidity value within an ambient environment over a period of time. The average ambient humidity value over the period of time is determined based on the average rate of change over the period of time of the electrolyte concentration within the electrolyte gas sensor of the gas detection apparatus over the period and the average temperature in the ambient environment over the period of time. The gas sensing apparatus may be configured to communicate the average ambient humidity value within the ambient environment to a second electrochemical gas sensor or a second gas detection apparatus within the same ambient environment.

17 Claims, 12 Drawing Sheets

(51) Int. Cl.
*G01K 1/14* (2021.01)
*G01N 27/413* (2006.01)

(56) References Cited

FOREIGN PATENT DOCUMENTS

WO 2018/059717 A1 4/2018
WO 2018/059719 A1 4/2018

OTHER PUBLICATIONS

China Application No. 202010267142.X Notification to Grant Patent Right dated Jun. 15, 2022 with English translation (7 pages).
Extended European Search Report Application No. 21178715.5 dated Sep. 15, 2021, 8 pages., dated Sep. 15, 2021.
Decision to grant a European patent received for European Application No. 20167850.5, dated Aug. 26, 2021, 2 pages.
European Search Report and Search Opinion received for EP Application No. 21178715.5, dated Sep. 15, 2021, 8 pages.
Corrected Notice of Allowability (PTOL-37) dated Apr. 29, 2021 for U.S. Appl. No. 16/376,624.
EPO computer-generated English language translation of the Description section of Shimada et al. JP 2017062195 A, patented Mar. 30, 2017, translation downloaded Janaury 30, 2021 (Year: 2017).
Extended European Search Report for Patent Application No. 20167850.5 dated Aug. 8, 2020, 5 pages.
Intention to Grant issued in European Application No. 20167850.5 dated Apr. 15, 2021, 49 pages.
Notice of Allowance and Fees Due (PTOL-85) dated Feb. 10, 2021 for U.S. Appl. No. 16/376,624.
Notice of Allowance and Fees Due (PTOL-85) dated May 10, 2021 for U.S. Appl. No. 16/376,624.
Notice of Publication and Entry Into Examination Stage issued in Chinese Application No. 202010267142.x dated Oct. 26, 2020, 2 pages.
Intention to grant dated Jul. 13, 2023 for EP Application No. 21178715, 9 pages(s).

\* cited by examiner

METHOD AND APPARATUS FOR MEASURING HUMIDITY USING AN ELECTROCHEMICAL GAS SENSOR

CROSS-REFERENCE TO RELATED APPLICATIONS

This patent application is a continuation of U.S. application Ser. No. 16/376,624, filed Apr. 5, 2019 and entitled "Method and Apparatus for Measuring Humidity Using an Electrochemical Gas Sensor," which is incorporated herein by reference in its entirety.

FIELD OF THE INVENTION

Various embodiments described herein relate generally to electrochemical gas sensors. In particular, various embodiments are directed to electrolyte-based gas sensors configured for measuring ambient humidity.

BACKGROUND

Industrial and commercial applications may use electrolyte-based electrochemical gas sensors to detect the presence of various gasses. The ambient humidity present within a conventional electrolyte-based electrochemical gas sensor's environment may cause a change in the sensor's electrolyte concentration due to water uptake or water loss with the ambient environment. The resulting change in electrolyte concentration affects the performance of the sensor, often leading to inaccurate sensor measurement, decreased measurement sensitivity, and even sensor failure. For this reason, some electrolyte-based electrochemical gas sensors incorporate conventional humidity sensors to measure ambient humidity and compensate for the resulting change in electrolyte concentration in order to appropriately calibrate the sensor's output. Conventional humidity sensors, however, are often expensive and bulky, thus increasing both the production costs and the footprint associated with the collective sensory components. Further, existing humidity sensors used in this context often produce unreliable readings and have relatively short lifespans-particularly when exposed to humidity extremes-compared to electrochemical gas sensors.

Accordingly, there is a need in the art for electrochemical gas sensors equipped with a reliable, long-lasting solution for measuring humidity characterized by lower product costs and a minimized sensor footprint.

BRIEF SUMMARY

Various embodiments relate to methods and apparatuses for reliably measuring humidity using an electrolyte-based electrochemical gas sensor.

Various embodiments are directed to a method for detecting gas using an electrochemical gas sensor and a gas detection apparatus comprising a first electrolyte-based electrochemical gas sensor configured to measure an electrolyte concentration within the first electrochemical gas sensor; a temperature sensor configured to measure a temperature of an ambient environment surrounding the first electrolyte-based electrochemical gas sensor; and a controller in communication with the first electrolyte-based electrochemical gas sensor and the temperature sensor, wherein the controller may be configured to (i) determine an average ambient temperature of the ambient environment over a first period of time, (ii) determine an average rate of change of electrolyte concentration within the first electrochemical gas sensor over the first period of time, and (iii) determine, based on the average ambient temperature and the average rate of change of electrolyte concentration, an average humidity value of the ambient environment over the first period of time.

In various embodiments, the first electrochemical gas sensor may comprise a volume of acid-based electrolyte. Further, in various embodiments, the controller of the gas detection apparatus may be configured to determine an average electrolyte vapor pressure over a period of time. In various embodiments, the temperature sensor may be integrated into the first electrochemical gas sensor. In various embodiments, a gas detection apparatus housing, wherein the gas detection apparatus housing may comprise an exterior housing portion and an interior housing portion, and wherein the first electrochemical gas sensor, the temperature sensor, and the controller may be enclosed within the interior housing portion.

In various embodiments, the average humidity value of the ambient environment over the first period of time may be determined using a look-up table correlating the average rate of change of electrolyte concentration within the first electrochemical gas sensor over the first period of time to a corresponding humidity value at the average ambient temperature and an average electrolyte vapor pressure within the first electrochemical gas sensor over the first period of time. Further, in various embodiments, the corresponding humidity value may define the average humidity value of an ambient environment over the first period of time.

In various embodiments, a gas detection apparatus may further comprise a second electrochemical gas sensor, wherein the second electrochemical gas sensor may be an electrolyte-based electrochemical gas sensor positioned within the ambient environment, and wherein the first electrochemical gas sensor may be configured to communicate the average humidity value of the ambient environment over the first period of time to the second electrochemical gas sensor. In various embodiments, the second electrochemical gas sensor may comprise a volume of non-acid-based electrolyte. Further in various embodiments, the second electrochemical gas sensor may be configured to apply an appropriate compensation factor to an output of the second electrochemical gas sensor based on the average humidity value of the ambient environment over the first period of time.

BRIEF DESCRIPTION OF THE DRAWINGS

Reference will now be made to the accompanying drawings, which are not necessarily drawn to scale, and wherein.

DETAILED DESCRIPTION

Figure 1:
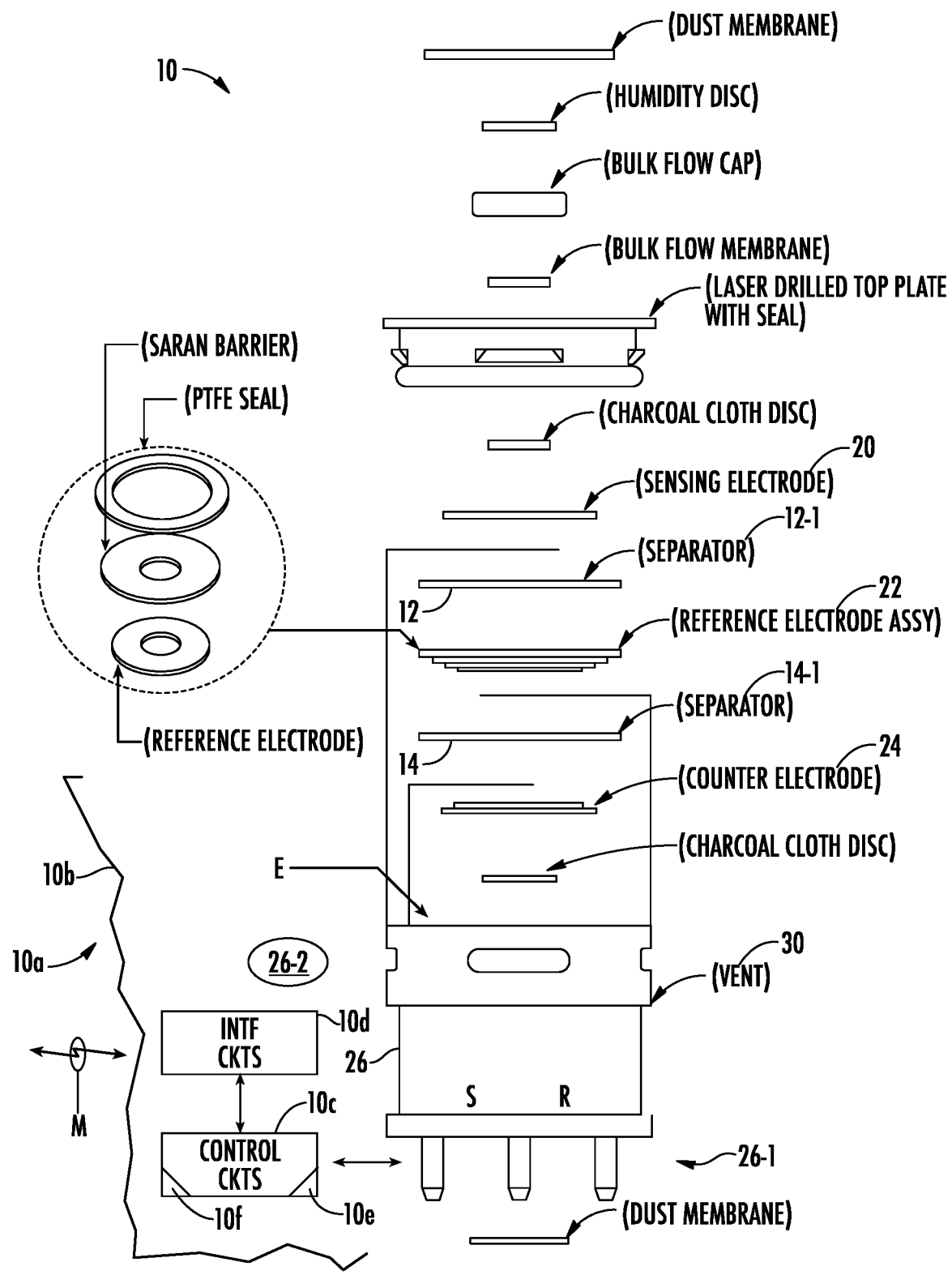
FIG. 1 illustrates an exploded view of a gas sensor according to one embodiment.

The following description should be read with reference to the drawings wherein like reference numerals indicate like elements throughout the several views. The detailed description and drawings show several embodiments which are meant to be illustrative of the disclosure. It should be understood that any numbering of disclosed features (e.g., first, second, etc.) and/or directional terms used in conjunction with disclosed features (e.g., front, back, top, bottom, side, and the like) are relative terms indicating illustrative relationships between the pertinent features.

It should be understood at the outset that although illustrative implementations of one or more aspects are illustrated below, the disclosed assemblies, systems, and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents. While values for dimensions of various elements are disclosed, the drawings may not be to scale.

The words "example," or "exemplary," when used herein, are intended to mean "serving as an example, instance, or illustration." Any implementation described herein as an "example" or "exemplary embodiment" is not necessarily preferred or advantageous over other implementations.

Overview

Described herein is a method and apparatus for reliably measuring humidity using an electrolyte-based electrochemical gas sensor. Electrochemical gas sensors that operate based on aqueous electrolytes (e.g., acid-based electrolytes) may exhibit changes in electrolyte concentration due to water uptake or water loss with the ambient environment. In particular, the concentration of aqueous electrolyte in electrolyte-based electrochemical gas sensors may vary in response to the ambient humidity. Accordingly, it may be desirable to characterize the average humidity of a sensor's ambient environment over a period of time in order to characterize that sensor's change in electrolyte concentration. The method and apparatus disclosed herein provides a solution for determining the average humidity value for an ambient environment over a period of time using a measured change in the electrolyte concentration of an electrochemical gas sensor and the measured average ambient temperature over that period of time.

As described herein, the method and apparatus disclosed may advantageously measure humidity based in part on a rate of change in electrolyte concentration within an electrochemical gas sensor. The disclosed methods and apparatuses therefore eliminate the need for separate humidity sensors in order to appropriately compensate the readings of such sensors based on ambient relative humidity. Additionally, the disclosed methods and apparatuses enable the measurement of relative humidity with an increased degree of reliability and may result in an increased sensor lifespan. Further, by determining humidity using existing hardware of an electrochemical gas sensor, the method and apparatus described herein will minimize the sensor's footprint and ultimately save production costs.

In one exemplary embodiment, a method for determining humidity using an electrochemical gas sensor may further comprise using the determined average humidity value over a period of time in order to determine the change in electrolyte concentration for those types of electrochemical gas sensor in which the electrolyte concentration may be difficult to determine (e.g., those that do not utilize an acid-based electrolyte). For example, it can be difficult, if not impossible, to measure changes in electrolyte concertation for electrolyte-based electrochemical gas sensors utilizing non-acid-based electrolytes (e.g., salt-based electrolytes, ionic liquid-type electrolytes, organic electrolytes). According to various embodiments, average humidity values determined from acid-based electrochemical gas sensors are therefore used to compensate for the measurements of non-acid based electrochemical gas sensors. In such embodiments, the overall accuracy of a system utilizing both acid-based and non-acid-based sensors can therefore be improved.

Apparatus

In various embodiments, as disclosed herein a gas detection apparatus 100 may comprise an electrochemical gas sensor and a controller configured to determine the average humidity over a period of time by measuring the electrolyte concentration within the electrochemical gas sensor and the temperature of the gas sensor's ambient environment over the given period of time.

FIG. 1 illustrates an exploded view of an exemplary electrochemical sensor 10 that may be used in accordance with the various embodiments of the apparatus and method described herein. Micro-electrodes 12, 14 are installed in sensor 10 at the positions shown at separator 12-1 near a working electrode 20 (which may also be known as a sensing electrode), and at separator 14-1 between the reference and counter electrodes 22, 24.

Electrolyte E is contained in the housing 26. Micro-electrodes 12, 14 are immersed in the electrolyte E, and are not in the direct path of the target gas.

The above described electrodes such as 12, 14, 20, 22, and 24 along with the electrolyte E are carried in a housing 26. Housing 26 can include a vent 30 as would be understood by those of skill in the art. Sensor 10 can be carried by a gas detector 10a, in an external housing 10b.

Electrical connecting elements, indicated at 26-1, carried by housing 26 are coupled to the various electrodes in the housing 26. A power supply 26-2, which could be implemented as a rechargeable battery, could be carried in external housing 10b to energize the gas detector 10a.

External housing 10b can also carry control circuits 10c which are coupled to the connector elements 26-1 to receive signals from and coupled signals to the electrodes 20, 22, 24 so as to sense conditions in the sensor 10, or to control the operation of one or more electrodes 20, 22, 24 to carry out the operational and diagnostic methods described herein.

The gas detector 10a can communicate via interface circuits 10d, coupled to control circuits 10c, via a medium M (which could be wired, or wireless), with displaced monitoring systems. The control circuits 10c can be implemented, at least in part, with a programmable processor 10e which executes pre-stored control instructions 10f. In various embodiments, the processor may be configured to receive sensory readings measuring, for example, temperature, pressure, and electrolyte concentration.

Exemplary micro-electrodes can be fabricated from PTFE coated platinum wire (Advent research materials part number PT5431, comprising 75μm diameter platinum wire with approximately 18μm thick PTFE coating). In some embodiments, the micro-electrodes 12, 14 may comprise a 50μm diameter platinum wire that is approximately 6 mm long and immersed in the electrolyte E. The wire can be cut with a scalpel to produce a microdisc electrode inside the sensor 10, and the PTFE insulation stripped from the end of the wire external to the sensor 10 to allow electrical contact to be made. The exposed tip of the wire can be pushed into the respective separators 12-1, 14-1 to avoid it shorting against the adjacent electrodes 20, 22 24. However an alternative approach includes sandwiching the micro-electrodes 12, 14 between two separators. Other configurations come within the spirit and scope of the invention. For example, the micro-electrodes may comprise uninsulated platinum wire and may operate as micro-cylinder electrodes, or they may be formed by deposition of platinum onto a contact pin or pad by techniques such as electroplating or sputtering, or by thick film printing platinum onto a ceramic substrate. In some embodiments, each micro-electrode 12, 14 may be used for separate diagnostic purposes, such as hydrogen peak reference, oxygen peak identification, etc. In various embodiments, an exemplary micro-electrode may be fabricated by welding a piece of platinum wire that may comprise, for example, a diameter between 25 um and 75 um (e.g., 50 um) and a substantially small length (e.g., 1 mm) to an end of an electrochemically inert supporting wire comprised of a suitable material (e.g., tantalum).

In some embodiments, scanning voltammetry may be completed on one or more of the micro-electrodes 12, 14 to provide one or more diagnostic scans. Scanning voltammetry is an electrochemical technique which measures the current that develops in an electrochemical cell under conditions where voltage is in excess of that predicted by the Nernst equation. Voltammetry is performed by cycling the potential of an electrode, and measuring the resulting current. In scanning voltammetry, the electrode potential may ramp linearly versus time in cyclical phases. In some embodiments, other waveforms may be used to complete the scanning voltammetry. For example, the waveform may be a stepped staircase (staircase voltammetry) or a staircase with additional superimposed positive and negative steps (square wave voltammetry). The rate of voltage change overtime during each of these phases is known as the experiment's scan rate (V/s). The results of a scanning voltammetry scan on one or more of the micro-electrodes 12, 14 may generate diagnostic information about the sensor 10.

Figure 2:
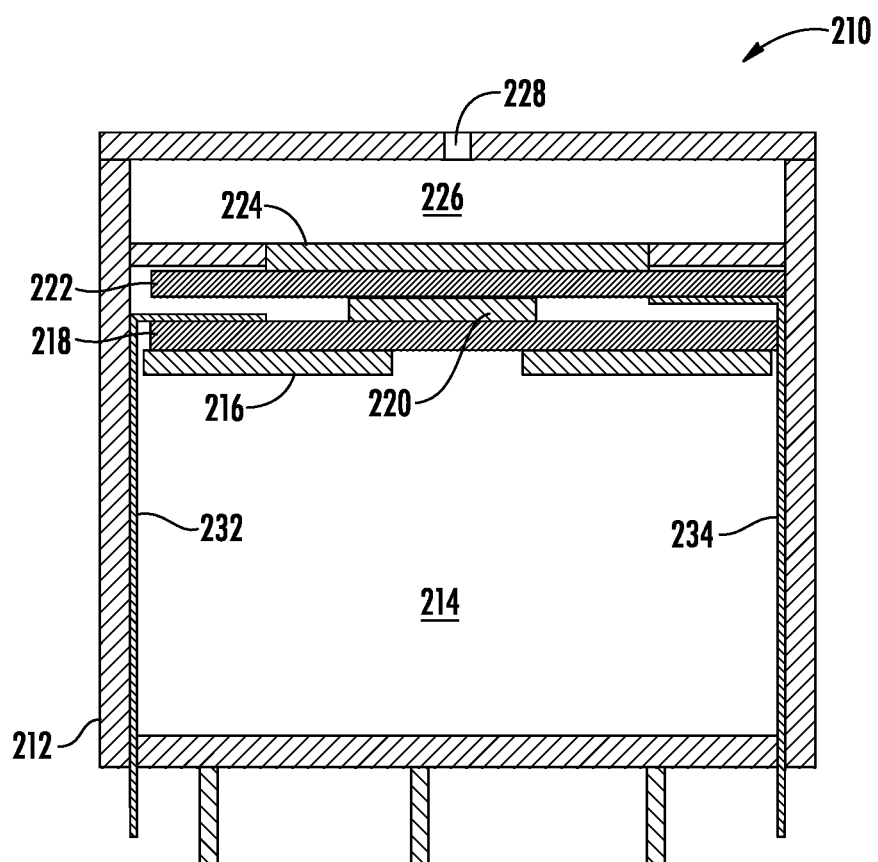
FIG. 2 schematically illustrates a cross-section drawing of an electrochemical sensor according to one embodiment.

FIG. 2 illustrates a cross-section drawing of an electrochemical sensor 210. The sensor 210 generally comprises a housing 212 defining a cavity or reservoir 214 designed to hold an electrolyte solution. A working electrode 224 can be placed between an opening 228 and the reservoir 214. A counter electrode 216 and a reference electrode 220 can be positioned within the reservoir 214. When the gas reacts at the interface between the working electrode 224 and the electrolyte within the separator 222, an electrical current and/or potential can be developed between the electrodes 216, 220 to provide an indication of the concentration of the gas. A reference electrode 220 may also be positioned within the reservoir 214 to provide a reference for the potential at the working electrode.

The housing 212 defines the interior reservoir 214, and one or more openings 228 can be disposed in the housing 212 to allow a gas to be detected to enter the housing 212 into a gas space 226. The housing 212 can generally be formed from any material that is substantially inert to the electrolyte and gas being measured. In an embodiment, the housing 212 can be formed from a polymeric material, a metal, or a ceramic. For example, the housing can be formed from a material including, but not limited to, acrylonitrile butadiene styrene (ABS), polyphenylene oxide (PPO), polystyrene (PS), polypropylene (PP), polyethylene (PE) (e.g., high density polyethylene (HDPE)), polyphenylene ether (PPE), or any combination or blend thereof. One or more openings 228 can be formed through the housing 212 to allow the ambient gas to enter the gas space 226 and/or allow any gases generated within the housing 212 to escape. In an embodiment, the electrochemical sensor 210 may comprise at least one inlet opening 228 to allow the ambient gas to enter the housing 212. The opening 228 can be disposed in a cap when a cap is present and/or in a wall of the housing 212. In some embodiments, the opening 228 can comprise a diffusion barrier to restrict the flow of gas (e.g., carbon monoxide, hydrogen sulfide, oxygen, etc.) to the working electrode 224. The diffusion barrier can be created by forming the opening 228 as a capillary, and/or a film or membrane can be used to control the mass flow rate through the one or more openings 228.

In an embodiment, the opening 228 may serve as a capillary opening to provide a rate limited exchange of the gases between the interior and exterior of the housing 212. In an embodiment, the opening 228 may have a diameter between about 200μm and about 1.5 mm, where the opening 228 can be formed using a conventional drill for larger openings and a laser drill for smaller openings. The opening 228 may have a length between about 0.5 mm and about 5 mm, depending on the thickness of the cap or housing 212. In some embodiments, two or more openings may be present for the inlet gases. When a membrane is used to control the gas flow into and/or out of the housing, the opening diameter may be larger than the sizes listed above as the film can contribute to and/or may be responsible for controlling the flow rate of the gases into and out of the housing 212.

The reservoir 214 comprises the counter electrode 216, the reference electrode 220, and the working electrode 224. In some embodiments, the electrolyte can be contained within the reservoir 214, and the counter electrode 216, the reference electrode 220, and the working electrode 224 can be in electrical contact through the electrolyte. In some embodiments, one or more porous separators 218, 222 or other porous structures can be used to retain the electrolyte in contact with the electrodes 216, 220, 224. The separators 218, 222 can comprise a porous member that acts as a wick for the retention and transport of the electrolyte between the reservoir 214 and the electrodes 216, 220, 224 while being electrically insulating to prevent shorting due to direct contact between any two electrodes. One or more of the porous separators 218, 222 can extend into the reservoir 214 to provide the electrolyte a path to the electrodes 216, 220, 224. In an embodiment, a separator 218 can be disposed between the counter electrode 216 and the reference electrode 220, and a separator 222 can be disposed between the reference electrode 220 and the working electrode 224.

One or more of the separators 218, 222 can comprise a nonwoven porous material (e.g., a porous felt member), a woven porous material, a porous polymer (e.g., an open cell foam, a solid porous plastic, etc.), or the like, and is generally chemically inert with respect to the electrolyte and the materials forming the electrodes. In an embodiment, the separators 218, 222 can be formed from various materials that are substantially chemically inert to the electrolyte including, but not limited to, glass (e.g., a glass mat), polymer (plastic discs), ceramics, or the like.

The electrolyte can be any conventional aqueous acidic electrolyte such as sulfuric acid, phosphoric acid, or a neutral ionic solution such as a salt solution (e.g., a lithium salt such as lithium chloride, etc.), or any combination thereof. For example, the electrolyte can comprise sulfuric acid having a molar concentration between about 3 M to about 12 M. Since sulfuric acid is hygroscopic, the concentration can vary from about 10 to about 70 wt % (1 to 11.5 molar) over a relative humidity (RH) range of the environment of about 3 to about 95%. In an embodiment, the electrolyte can comprise phosphoric acid having a concentration in an aqueous solution between about 30% to about 60% H3PO4 by weight. As another example, the electrolyte can include a lithium chloride salt having about 30% to about 60% LiCl by weight, with the balance being an aqueous solution. As another example, a proton conducting ionic liquid may be used.

In some embodiments, the electrolyte may be in the form of a solid polymer electrolyte which comprises an ionic exchange membrane. In some embodiments, the electrolyte can be in the form of a free liquid, disposed in a matrix or slurry such as glass fibers (e.g., the separator 218, the separator 222, etc.), or disposed in the form of a semi-solid or solid gel.

The working electrode 224 may be disposed within the housing 212. The gas entering the sensor 210 can contact one side of the working electrode 224 and pass through working electrode 224 to reach the interface between the working electrode 224 and the electrolyte. The gas can then react to generate the current indicative of the gas concentration. As disclosed herein, the working electrode 224 can comprise a plurality of layers. The base or substrate layer can comprise a hydrophobic material or a hydrophobically treated material. A catalytic material can be formed as an electrode on one side of the working electrode 224 and placed in contact with the electrolyte.

In an embodiment, the working electrode 224 can comprise a porous substrate or membrane as the base layer. The substrate can be porous to the gas of interest, which in some embodiments can comprise hydrogen sulfide, carbon monoxide, or oxygen. In an embodiment, the substrate can comprise a carbon paper formed of carbon or graphite fibers. In some embodiments, the substrate can be made to be electrically conductive through the addition of a conductive material such as carbon. The use of carbon may provide a sufficient degree of electrical conductivity to allow the current generated by the reaction of the gas with the electrolyte at the surface of the working electrode 224 to be detected by a lead coupled to the working electrode 224. Other electrically conductive substrates may also be used such as carbon felts, porous carbon boards, and/or electrically conductive polymers such as polyacetylene, each of which may be made hydrophobic as described below. Alternatively, an electrically conductive lead can be coupled to the catalytic layer to electrically couple the catalytic material to the external circuitry, as described in more detail herein. In an embodiment, the substrate can be between about 5 mils to about 20 mils thick in some embodiments.

The porous substrate can be hydrophobic to prevent the electrolyte from passing through the working electrode 224. The substrate can be formed from a hydrophobic material, or the substrate can be treated with a hydrophobic material. In an embodiment, the substrate can be made hydrophobic through the impregnation of the substrate with a hydrophobic material such as a fluorinated polymer (e.g., PTFE, etc.). In some embodiments, the substrate or membrane can comprise GEFC-IES (e.g., the copolymer of perfluorosulfonic acid and PTFE, which is commercially available from Golden Energy Fuel Cell Co., Ltd.), Nafion® (a copolymer of polytetrafluoroethylene and perfluoro-3,6-dioxa-4-methyl-7-octene-sulfonic acid, which is commercially available from Dupont™), or pure or nearly pure polytetrafluoroethylene (PTFE). The impregnation process can include disposing a hydrophobic material containing solution or slurry on the substrate using a dipping, coating, or rolling process. Alternatively, a dry composition such as a powder can be applied to the substrate. In some embodiments, an optional sintering process can be used to infuse the hydrophobic material into the substrate to create the hydrophobic base layer for the working electrode 224, where both sides of the hydrophobic base layer are hydrophobic. The sintering process can cause the hydrophobic polymer to bond or fuse with the carbon of the substrate to securely bond the hydrophobic material to the substrate.

The resulting substrates can contain about 30% to about 50% by weight of the hydrophobic polymer. The amount of hydrophobic material added to the substrate can affect the electrical conductivity of the substrate, where the electrical conductivity tends to decrease with an increased amount of the hydrophobic material. The amount of the hydrophobic polymer used with the substrate may depend on the degree of hydrophobicity desired, the porosity to the target gas, and the resulting electrical conductivity of the working electrode.

The catalytic layer can be formed by mixing the desired catalyst with a binder and depositing the mixture on the substrate material. The binder can comprise a solution of perfluorinated ion electrolyte solution (e.g., GEFC-IES, Nafion®, etc.), a hydrophobic material such as PTFE, mixtures thereof, or the like. When used as a binder, the GEFC-IES Nafion® and/or PTFE can affect the gas diffusion parameters while supporting the electrocatalyst and maximizing the interfaces between catalyst, gas, and electrolyte at which the electrochemical processes occur. Glycol or other similar chemicals can be used as a diluent to form a catalyst slurry, recipe, or catalyst system, which can be printed on a substrate by a printer.

The catalytic layer might be deposited onto the substrate by, for example, screen printing, filtering in selected areas from a suspension placed onto the substrate, by spray coating, or any other method suitable for producing a patterned deposition of solid material. Deposition might be of a single material or of more than one material sequentially in layers, so as, for example, to vary the properties of the electrode material through its thickness or to add a second layer of increased electrical conductivity above or below the layer which is the main site of gas reaction. Once deposited, the printed element can be sintered at an elevated temperature to form the electrode.

In the working electrode 224, the catalytic layer can comprise carbon (e.g., graphite) and/or one or more metals or metal oxides such as copper, silver, gold, nickel, palladium, platinum, ruthenium, iridium, and/or oxides of these metals. The catalyst used can be a pure metal powder, a metal powder combined with carbon, or a metal powder supported on an electrically conductive medium such as carbon, or a combination of two or more metal powders either as a blend or as an alloy. The materials used for the individual electrodes can be the same or different. In an embodiment, the working electrode 224 comprises a platinum-ruthenium black (Pt—Ru black) electrode. The atomic ratio of the Pt to Ru in the Pt—Ru black electrode can be in the range of about 1:1 to about 1:5, or about 1:2. The catalyst material can have a weight loading per square centimeter (cm<2>) of the surface area of the working electrode 224 of between about 0.1 mg/cm<2> and about 5 mg/cm<2>, or between about 0.5 mg/cm<2> and about 2 mg/cm<2>, or about 1 mg/cm<2>.

The counter electrode 216 can be disposed within the housing 212. The counter electrode 216 can comprise a substrate or membrane such as a PTFE membrane, a GEFC-IES membrane, a Nation® membrane, or the like having a catalytic material disposed thereon. In an embodiment, the catalytic material can be mixed and disposed on the membrane using any suitable process such as rolling, coating, screen printing, or the like to apply the catalytic material on the membrane, as described in more detail herein. The catalyst layer can then be bonded to the membrane through a sintering process as described herein.

In an embodiment, the catalytic material for the counter electrode can comprise a noble metal such as gold (Au), platinum (Pt), ruthenium (Ru), rhodium (Rh), Iridium (Ir), oxides thereof, or any combination thereof. In an embodiment, the catalytic material comprises a Pt—Ru mixture that is screen printed on the membrane, where the membrane can be a GEFC-IES membrane. The catalyst loading for the counter electrode 216 can be within any of the ranges described herein for the working electrode 224. In an embodiment, the catalyst loading for the counter electrode 216 can be the same or substantially the same as the catalyst loading for the working electrode 224, the catalyst loading can also be greater than or less than that of the working electrode 224. Similarly, the reference electrode 220 can be disposed within the housing 212. The reference electrode 220 can comprise a substrate or membrane such as a PTFE membrane, a GEFC-IES membrane, a Nafion® membrane, or the like having a catalytic material disposed thereon. In an embodiment, the catalytic material can be mixed with a hydrophobic material (e.g., PTFE, etc.) and disposed on the PTFE membrane. Any of the methods used to form the working electrode or the counter electrode can also be used to prepare the reference electrode 220. In an embodiment, the catalytic material used with the reference electrode 220 can comprise a noble metal such as gold (Au), platinum (Pt), ruthenium (Ru), rhodium (Rh), Iridium (Ir), oxides thereof, or any combination thereof. In an embodiment, the catalytic material used to form the reference electrode 220 can comprise a Pt—Ru mixture that is screen printed on the membrane, where the membrane can be a GEFC-IES membrane. The catalyst loading for the reference electrode 220 can be within any of the ranges described herein for the working electrode 224. In an embodiment, the catalyst loading for the reference electrode 220 can be the same or substantially the same as the catalyst loading for the working electrode 224, the catalyst loading can also be greater than or less than that of the working electrode 224. While illustrated in FIG. 1 as having the reference electrode 220, some embodiments of the electrochemical sensor may not include a reference electrode 220.

In order to detect the current and/or potential difference across the electrodes in response to the presence of the target gas, one or more leads or electrical contacts can be electrically coupled to the working electrode 224, the reference electrode 220, and/or the counter electrode 216. The lead contacting the working electrode 224 can contact either side of the working electrode 224 since the substrate comprises an electrically conductive material. In order to avoid the corrosive effects of the electrolyte, the lead contacting the working electrode 224 can contact the side of the working electrode 224 that is not in contact with the electrolyte. Leads may be similarly electrically coupled to the counter electrode 216 and the reference electrode 220. The leads can be electrically coupled to external connection pins to provide an electrical connection to external processing circuitry. The external circuitry can detect the current and/or potential difference between the electrodes and convert the current into a corresponding target gas concentration.

In some embodiments, the sensor 210 may comprise one or more diagnostic micro-electrodes 232 and 234 (which may be similar to the micro-electrodes 12, 14 of FIG. 1). The diagnostic electrode may be a wire (as shown in FIG. 2), where the exposed tip of the wire can be pushed into the separators 222, 218 to avoid it shorting against the adjacent electrodes. However an alternative approach includes sandwiching the micro-electrodes 232, 234 between two separators. Other configurations come within the spirit and scope of the invention. For example, the micro-electrodes may comprise uninsulated platinum wire and may operate as micro-cylinder electrodes, or they may be formed by deposition of platinum onto a contact pin or pad by techniques such as electroplating or sputtering, or by thick film printing platinum onto a ceramic substrate. In some embodiments, each micro-electrode 232, 234 may be used for separate diagnostic purposes, such as hydrogen peak reference, oxygen peak identification, etc. The micro-electrodes may comprise platinum, gold, ruthenium, rhodium, iridium, palladium, rhenium, osmium, or their alloys with each other or with other metals (e.g. platinum/nickel alloys).

In use, the sensor 210 can detect a target gas concentration. In use, the ambient gas can flow into the sensor 210 through the opening 228, which serves as the intake port for the sensor 210. The ambient gas can comprise a concentration of the target gas, which may include hydrogen sulfide, oxygen, and/or carbon monoxide. The gas can contact the working electrode 224 and pass through the fine pores of the porous substrate layer to reach the surface of the working electrode 224 treated with the catalyst layer. The electrolyte may be in contact with the surface of the working electrode 224, and the target gas may react and result in an electrolytic current forming between the working electrode 224 and the counter electrode 216 that corresponds to the concentration of the target gas in the ambient gas. By measuring the current, the concentration of target gas can be determined using, for example, the external detection circuitry.

In some embodiments of the disclosure, one or more elements of the sensor (as described above in FIGS. 1 and 2) may be scanned using scanning voltammetry to observe the effects of changing concentration in the electrolyte (E above).

An electrochemical sensor may be scanned using one or more of the electrodes. In some embodiments, the scanning may be done on a micro-electrode within the sensor. The scan may generate a graph that contains a plurality of peaks due to adsorption, desorption, formation, and/or reduction of certain elements. The scanning may be completed at a plurality of electrolyte concentrations, wherein the graphs for each of the concentrations may be compared. In some embodiments, the graph may show one or more peaks that are consistent for each concentration, which may be considered reference peaks. Additionally, the graph may show one or more peaks that change with concentration. The difference in voltage between the concentration dependent peak(s) and the reference peak(s) may provide a correlation for electrolyte concentration. This correlation may approximately linear when the axes of the graph are electrolyte concentration and voltage difference between the two peaks.

Once a correlation is established, the electrolyte concentration for similar electrochemical sensors may be determined by completing a voltammetry scan on the sensor, and then identifying the relevant peaks to the correlation. Once the voltage difference between the peaks is identified, the electrolyte concentration may be determined. The determined electrolyte concentration may be used to correct sensor readings, and/or to identify any other errors with the sensor.

In some embodiments, a diagnostic micro-electrode may be used to complete the voltammetry scans. The benefits to using a micro-electrode may be that it would be lower power, require a shorter measurement time, suffers less distortion of the measurement due to ohmic losses in the electrolyte, and it avoids disturbing the main gas working electrode.

The disclosure having been generally described, the following examples are given as particular embodiments of the disclosure and to demonstrate the practice and advantages thereof. It is understood that the examples are given by way of illustration and are not intended to limit the specification or the claims in any manner.

Figure 3:
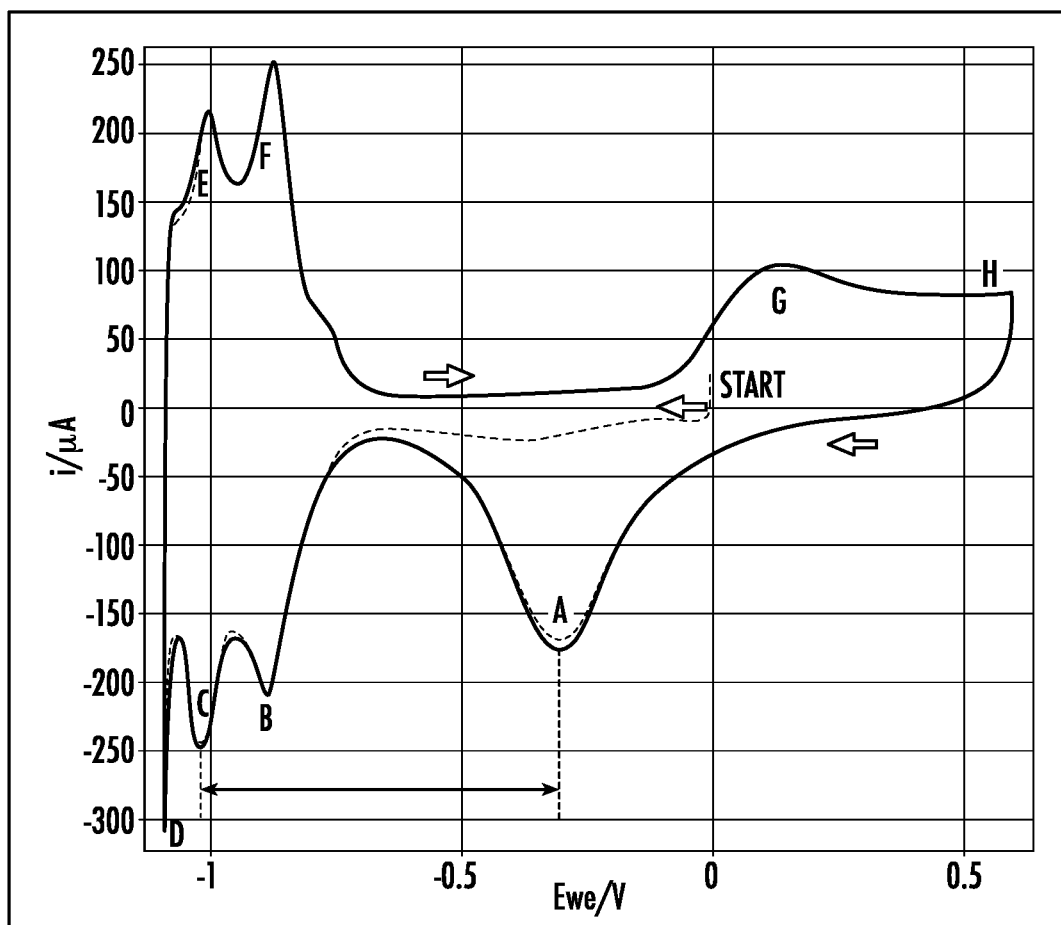
FIG. 3 illustrates a graph of current vs. potential according to one embodiment.

FIG. 3 illustrates a staircase voltammogram of an exemplary electrode. To investigate the effects of the changing concentration of electrolyte in the sensor cells, scanning voltammetry may be performed in a range of H2SO4 solutions (0.6 M, 2.5 M, 5 M, 8 M, 10 M, and 12 M) and the results are shown in FIG. 3. In other words, using the same electrode, acid concentration was varied between 0.6 M and 12 M.

The staircase voltammogram shown in FIG. 3 illustrates a plot generated from an exemplary micro-electrode that comprises a 50μm diameter platinum wire approximately 6 mm long immersed in electrolyte. The scanning was completed at 5 V/s, with 2 mV steps, and 100% charge integration. The sensor was galvanostatically scanned 10 times between hydrogen (H2) and oxygen (O2) evolution to clean the electrode prior to voltammetry scanning. The wire micro-electrode was driven relative to usual platinum reference and counter electrodes.

As shown in FIG. 3, hydrogen peaks (B, C, E, and F) occur at a well-defined potential and therefore can be used as a standard reference, where peak (C) is the most well-defined. The peaks indicating oxide formation (G) and reduction (A) appear to be electrolyte concentration dependent, where peak (G) is not always well defined. However peak (A) is always clear and easy to detect but its position varies with anodic swing (H). Therefore, to determine a correlation, the anodic swing (H) may be fixed relative to the hydrogen peak (C) so that the voltage difference (i.e. V(A)–V(C)) is then a measure of electrolyte concentration. In the testing illustrated by FIG. 3, it was shown that the presence of oxygen does not interfere with the measurement.

Figure 4A:
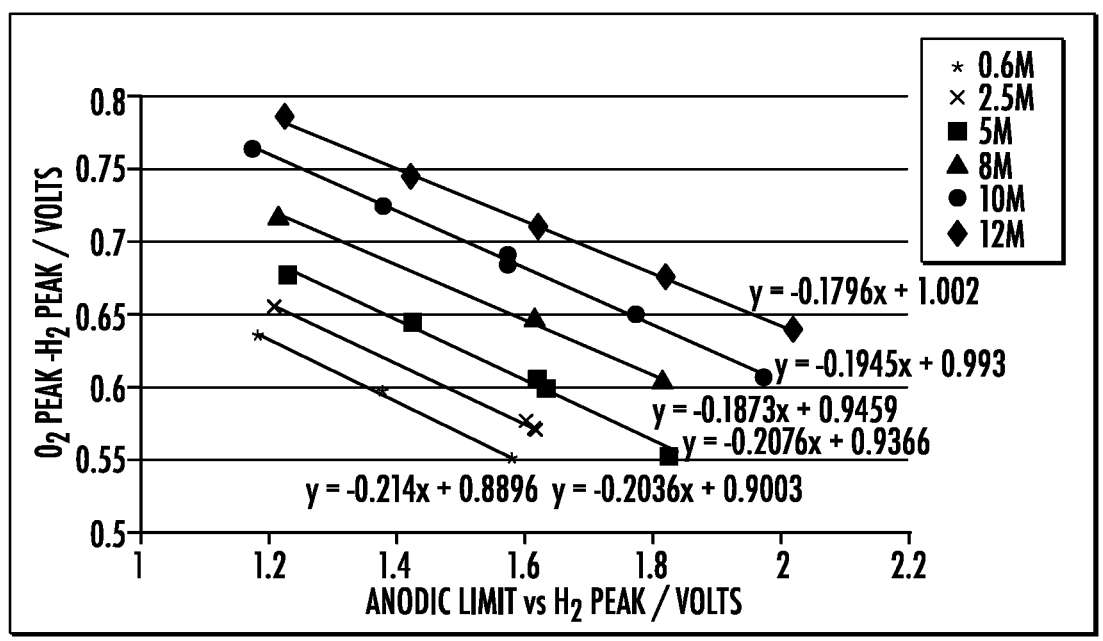
FIG. 4A illustrates a graph of potential difference vs. anodic swing according to one embodiment.
Figure 4B:
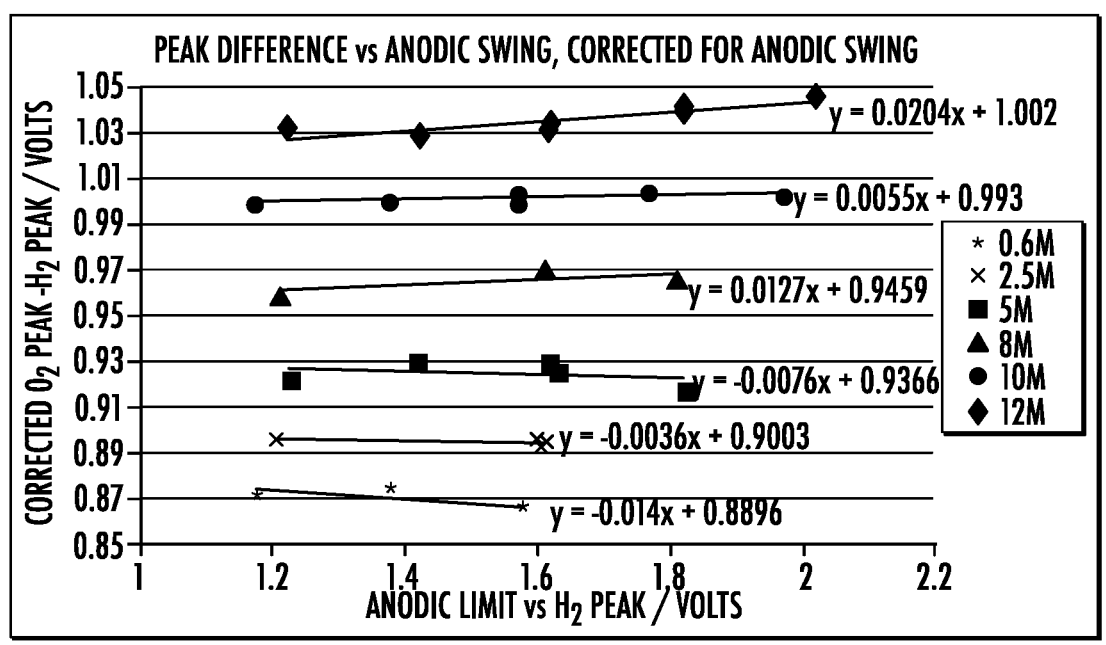
FIG. 4B illustrates a graph of potential difference vs. anodic swing, corrected for anodic swing, according to one embodiment.

FIG. 4A illustrates the oxide reduction peak position dependent on the anodic limit. The linear correlations are illustrated on the graph. To correct for the anodic limit, the slopes of the linear correlations may be adjusted. As shown in FIG. 4B a slope of approximately 0.2*x was applied to the data. FIG. 4B illustrates the correction for effects of the anodic limit. In another embodiment, the effect of the anodic limit may be accounted for when determining the peak difference, wherein anodic limit may be defined relative to the hydrogen reference peak.

Figure 4C:
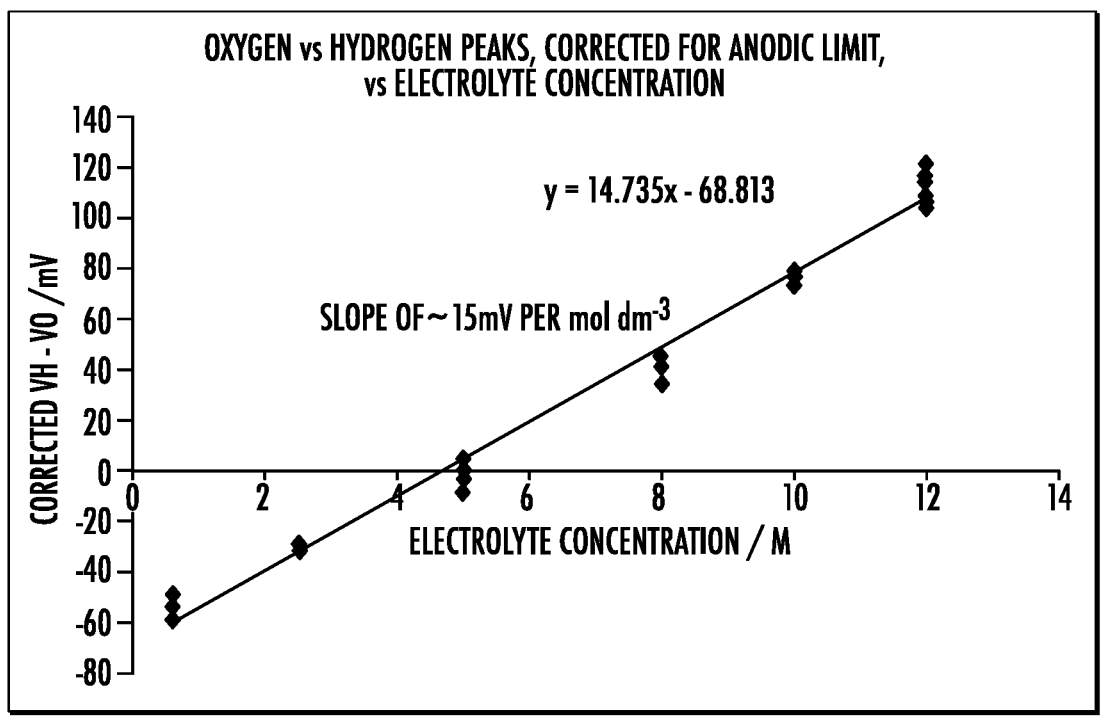
FIG. 4C illustrates a graph of potential difference vs. concentration of the electrolyte according to one embodiment.

FIG. 4C illustrates the corrected peak difference values as a function of electrolyte concentration. FIG. 4C shows that there is a strong correlation between the potential difference between the two peaks (oxide reduction and adsorbed hydrogen) and the concentration of the electrolyte. Therefore, this measurement could therefore be used as an indicator of the concentration of the electrolyte. Additionally, the potential appears to be linearly dependent on electrolyte concentration over the full range of environmental interest (0.6 M-12 M).

In some embodiments, temperature may have an effect on the electrolyte concentration measurement by diagnostic micro-electrode. The effect may be small and may be easily compensated for by using a low accuracy temperature sensor. As an example, the observed peak separation increased by around 1 mV/C, which may be equivalent to approximately 0.07 M/C.

In some embodiments, the voltammetry may be completed using square wave voltammetry (SWV). Using SWV may improve the definition of the hydrogen peaks over traditional staircase voltammetry. In some embodiments, both techniques may be used. For example, SWV may be used to determine the hydrogen peaks, and then subsequent staircase voltammetry may be used to determine the oxide reduction peak. Also, square wave voltammetry allows for detection of an additional peak for oxide formation (which is normally only a shoulder in voltammetry). This additional peak is also a function of both electrolyte concentration and temperature, so it could be used in addition to or instead of the oxide reduction peak. One benefit of using the above described method is that the position of the oxide formation peak (G) is not affected by the anodic limit since it is formed on the anodic scan, therefore it is not necessary to perform the correction shown in FIG. 4B or to control the anodic limit. A further benefit of using the oxide formation peak (G) is that it gives a measurement which is more sensitive to the electrolyte concentration and less sensitive to temperature. The following equations were obtained by fitting the results of square voltammetry on sensors of the design shown in FIG. 1, with a range of sulphuric acid concentrations from 7 to 14 M over a temperature range from 20 C to 50 C.

$$V(A-C)=552+0.582\times\text{Temperature}+10.44\times\text{Concentration}$$

$$V(G-C)=852+0.102\times\text{Temperature}+17.59\times\text{Concentration}$$

Where V(A–C) is the potential difference in millivolts between the oxide reduction peak and a hydrogen peak, V(G–C) is the potential difference in millivolts between the oxide formation peak and a hydrogen peak, temperature is in degrees Celsius and Concentration is in moles per liter. The use of the formation peak gives a more sensitive measure of the electrolyte concentration with less need for temperature compensation. Alternatively, the two equations can be solved simultaneously to allow both the concentration and temperature to be determined, avoiding the need for a separate temperature sensor to be present.

Square wave voltammetry adds additional parameters which can be adjusted to optimize the measurement. For example, variation of step height changes the intensities of the oxide peaks but does not affect the hydrogen peaks. So SWV could be used to optimize the peaks for ease of measurement or to help distinguish between the peak types, thereby simplifying the detection methods.

Figure 5:
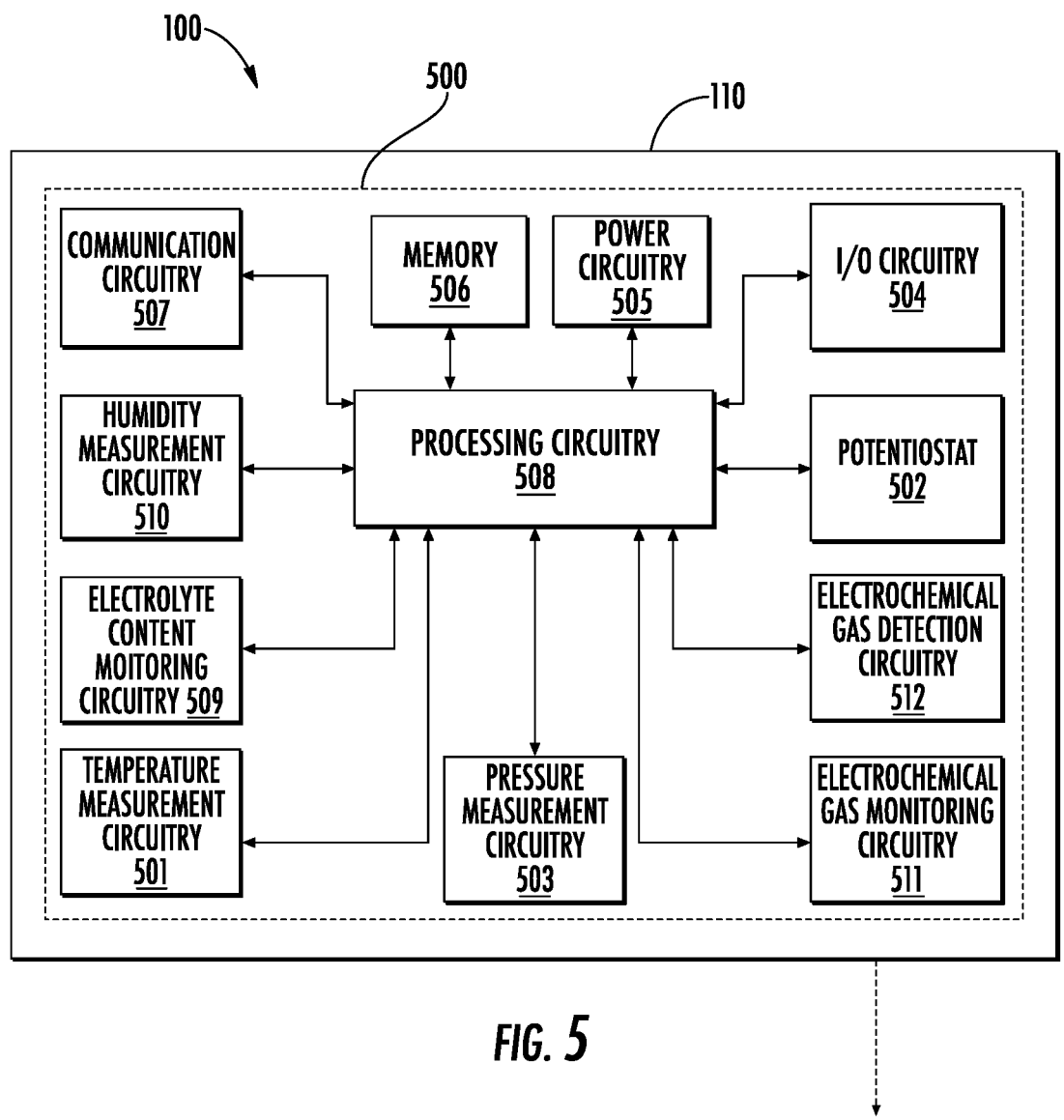
FIG. 5 illustrates an example schematic block diagram in accordance with some example embodiments described herein.

The example gas detection apparatus 100 described herein, such as controller 500 shown in FIG. 5. As illustrated in FIG. 5, the controller 500 may comprise a temperature measurement circuitry 501, and pressure measurement circuitry 503, processing circuitry 508, a potentiostat 502, input/output circuitry 504, power circuitry 505, memory 506, communication circuitry 507, humidity measurement circuitry 510, electrolyte content monitoring circuitry 509, electrochemical gas monitoring circuitry 511, and electrochemical gas detection circuitry 512.

The use of the term "circuitry" as used herein with respect to components of the gas detection apparatus 100 therefore includes particular hardware configured to perform the functions associated with respective circuitry described herein. Of course, while the term "circuitry" should be understood broadly to include hardware, in some embodiments, circuitry may also include software for configuring the hardware. For example, in some embodiments, "circuitry" may include processing circuitry, storage media, network interfaces, input-output devices, and other components. In some embodiments, other elements of the controller 500 may provide or supplement the functionality of particular circuitry. For example, the processing circuitry 508 may provide processing functionality, memory 506 may provide storage functionality, and communication circuitry 507 may provide network interface functionality, among other features.

The temperature measurement circuitry 501 includes hardware components designed or configured to receive, process, generate, and transmit data, such as ambient temperature data. In various embodiments, the temperature measurement circuitry 501 may be configured to measure the temperature of the ambient environment within which the gas detection apparatus 100 is located. In various embodiments, the temperature measurement circuitry 501 may be configured to measure the ambient temperature over one or more time intervals. Further, the temperature measurement circuitry 501 may be configured to determine the change in temperature or the average temperature over the one or more time intervals. In various embodiments, the temperature measurement circuitry 501 may be positioned either within or outside of the electrochemical gas sensor housing and may further be integrated into one or more components of the gas detection apparatus 100 (e.g., the electrochemical gas sensor).

The pressure measurement circuitry 503 includes hardware components designed or configured to receive, process, generate, and transmit data, such as electrolyte water vapor pressure data. In various embodiments, the pressure measurement circuitry 503 may be configured to determine the vapor pressure of an electrolyte present within the electrochemical gas sensor. In various embodiments, the electrolyte water vapor pressure may be a function of one or more of the measured electrolyte concentration values of the electrochemical gas sensor, the measured ambient temperature, and the total volume of water present within the electrochemical gas sensor. In various embodiments, the pressure measurement circuitry 503 may be configured to determine the electrolyte water vapor pressure over one or more time intervals. Further, the pressure measurement circuitry 503 may be configured to determine the change in electrolyte water vapor pressure or the average electrolyte water vapor pressure over the one or more time intervals. In various embodiments, the pressure measurement circuitry 503 may be positioned either within or outside of the electrochemical gas sensor housing and may further be integrated into one or more components of the gas detection apparatus 100 (e.g., the electrochemical gas sensor).

Figure 6:
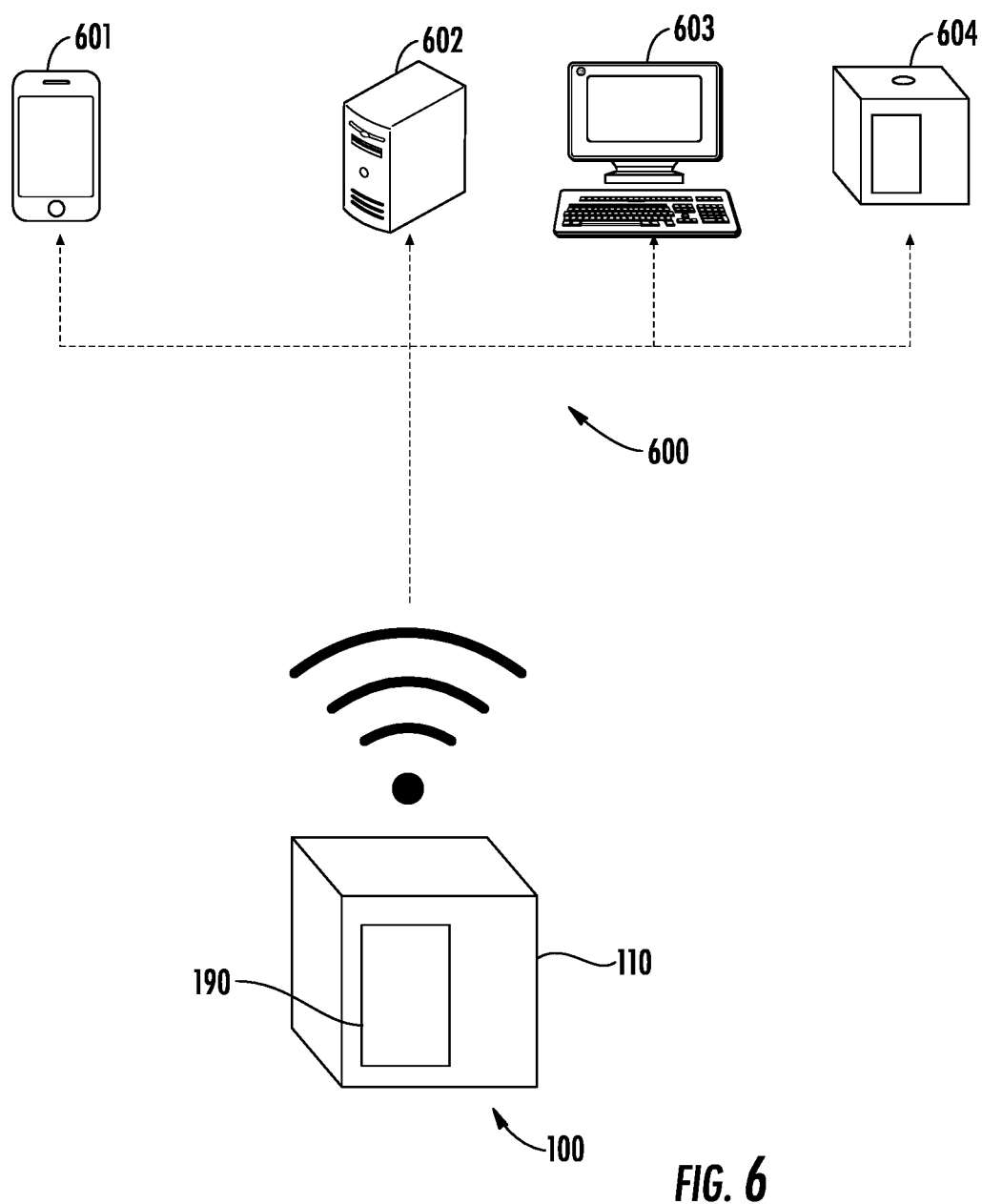
FIG. 6 illustrates data flows among components in accordance with some embodiments discussed herein.

In some embodiments, the controller 500 may include input-output circuitry 504 that may, in turn, be in communication with the processing circuitry 508 to provide output to the user and, in some embodiments, to receive input such as a command provided by the user. As shown in FIG. 6, the input-output circuitry 504 may comprise a user interface 190, such as a graphical user interface (GUI), and may include a display that may include a web user interface, a GUI application, a mobile application, a client device, or any other suitable hardware or software. In some embodiments, the input-output circuitry 504 may also include a keyboard, a mouse, a joystick, a display device, a display screen, a touch screen, touch areas, soft keys, a microphone, a speaker (e.g., a buzzer), a light emitting device (e.g., a red light emitting diode (LED), a green LED, a blue LED, a white LED, an infrared (IR) LED, an ultraviolet (UV) LED, or a combination thereof), or other input-output mechanisms. The processing circuitry 508, input-output circuitry 504 (which may utilize the processing circuitry), or both may be configured to control one or more functions of one or more user interface elements through computer-executable program code instructions (e.g., software, firmware) stored in a non-transitory computer-readable storage medium (e.g., memory 506). Input-output circuitry 504 is optional and, in some embodiments, the controller 500 may not include input-output circuitry. For example, where the controller 500 does not interact directly with the user, the controller 500 may generate user interface data for display by one or more other devices with which one or more users directly interact and transmit the generated user interface data to one or more of those devices. For example, the controller 500, using user interface circuitry may generate user interface data for display by one or more display devices and transmit the generated user interface data to those display devices In various embodiments, the power circuitry 505 may be configured to receive power and power gas detection apparatus 100. As non-limiting examples, the power circuitry 505 may comprise one or more batteries, one or more capacitors, one or more constant power supplies (e.g., a wall-outlet), and/or the like. In some embodiments, the power circuitry 505 may comprise an external power supply positioned outside of the apparatus housing 110 and configured to deliver alternating or direct current power to the gas detection apparatus 100. Further, in some embodiments, as illustrated in FIG. 5, the power circuitry 505 may comprise an internal power supply, for example, one or more batteries, positioned within the apparatus housing 110.

In some embodiments, the processing circuitry 508 (and/or co-processor or any other processing circuitry assisting or otherwise associated with the processor) may be in communication with the memory 506 via a bus for passing information among components of the apparatus. The memory 506 may be non-transitory and may include, for example, one or more volatile and/or non-volatile memories. For example, the memory 506 may be an electronic storage device (e.g., a computer readable storage medium). In another example, the memory 506 may be a non-transitory computer-readable storage medium storing computer-executable program code instructions that, when executed by a computing system, cause the computing system to perform the various operations described herein. The memory 506 may be configured to store information, data, content, signals applications, instructions (e.g., computer-executable program code instructions), or the like, for enabling the controller 500 to carry out various functions in accordance with example embodiments of the present disclosure. For example, the memory 506 may be configured to store electrolyte content monitoring techniques; capacitance measurement techniques; impedance measurement techniques; monitored data; ranges of monitored data; ranges of frequencies (e.g., band-gap filters); electrolyte content monitoring signals; temperature measurement signals, temperature measurement data, pressure measurement signals, pressure measurement data, water volume content data, humidity determination techniques, humidity measurement look-up tables, humidity measurement data, any other suitable data or data structures; or any combination or combinations thereof. It will be understood that the memory 506 may be configured to store partially or wholly any electronic information, data, data structures, embodiments, examples, figures, processes, operations, techniques, algorithms, instructions, systems, apparatuses, methods, or computer program products described herein, or any combination thereof. In various embodiments, a look-up table may be a data matrix used to define a relationship between a rate of change of electrolyte concentration over a first period of time to a corresponding humidity value at an ambient temperature and an electrolyte water vapor pressure. Further, a look-up table as described herein may correlate the average rate of change of electrolyte concentration within the first electrochemical gas sensor over the first period of time to a corresponding humidity value at the average ambient temperature and an average electrolyte water vapor pressure within the first electrochemical gas sensor over the first period of time, wherein the corresponding humidity value defines the average humidity value of an ambient environment over the first period of time.

The processing circuitry 508 may be embodied in a number of different ways and may, for example, include one or more processing devices configured to perform independently. Additionally or alternatively, the processing circuitry 508 may include one or more processors configured in tandem via a bus to enable independent execution of instructions, pipelining, multithreading, or a combination thereof. The use of the term "processing circuitry" may be understood to include a single core processor, a multi-core processor, multiple processors internal to the apparatus, remote or "cloud" processors, or a combination thereof.

In an example embodiment, the processing circuitry 508 may be configured to execute instructions stored in the memory 506 or otherwise accessible to the processing circuitry 508. Alternatively or additionally, the processing circuitry 508 may be configured to execute hard-coded functionality. As such, whether configured by hardware or software methods, or by a combination of hardware with software, the processing circuitry 508 may represent an entity (e.g., physically embodied in circuitry) capable of performing operations according to an embodiment of the present disclosure while configured accordingly. As another example, when the processing circuitry 508 is embodied as an executor of program code instructions, the instructions may specifically configure the processor to perform the operations described herein when the instructions are executed.

In various embodiments, the processing circuitry 508 may be further configured to control the potentiostat 502 to complete the voltammetry scans of the electrochemical gas sensor as described above.

The communication circuitry 507 may allow any of the sensory results or readings communicated to the processing circuitry 508 as discussed herein (e.g., electrochemical gas monitoring circuitry 511 output, temperature measurement circuitry 501 output, pressure measurement circuitry 503 output, humidity measurement circuitry 510 results) to be further communicated to an external source. The communication circuitry 507 may include, for example, a network interface for enabling communications with a wired or wireless communication network. For example, the communication circuitry 507 may include one or more network interface cards, antennae, buses, switches, routers, modems, and supporting hardware and/or software, or any other device suitable for enabling communications via a network. In some embodiments, the communication interface may include the circuitry for interacting with the antenna(s) to cause transmission of signals via the antenna(s) or to handle receipt of signals received via the antenna(s). These signals may be transmitted or received by the gas detection apparatus 100 using any of a number of Internet, Ethernet, cellular, satellite, or wireless technologies, such as IEEE 802.11, Code Division Multiple Access (CDMA), Global System for Mobiles (GSM), Universal Mobile Telecommunications System (UMTS), Long-Term Evolution (LTE), Bluetooth© v1.0 through v5.0, Bluetooth Low Energy (BLE), infrared wireless (e.g., IrDA), ultra-wideband (UWB), induction wireless transmission, Wi-Fi, near field communications (NFC), Worldwide Interoperability for Microwave Access (WiMAX), radio frequency (RF), RFID, or any other suitable technologies.

In various embodiments, the processing circuitry 508 may be configured to communicate with the humidity measurement circuitry 510. The humidity measurement circuitry 510 may include hardware components designed or configured to receive, process, generate, and transmit data, such as ambient humidity data. In various embodiments, the humidity measurement circuitry 510 may be configured to determine the humidity of the ambient environment within which the gas detection apparatus 100 is located. In various embodiments, the ambient humidity may be a function of one or more of the rate of change of electrolyte concentration within the electrochemical gas sensor, the measured ambient temperature, and the electrolyte water vapor pressure. In various embodiments, the humidity measurement circuitry 501 may be configured to determine the ambient humidity over one or more time intervals. Further, the humidity measurement circuitry 510 may be configured to determine the average ambient humidity over the one or more time intervals. In various embodiments, the humidity measurement circuitry 510 may be configured to determine the average ambient humidity over a period of time by retrieving electrolyte concentration data defining the average rate of change of electrolyte concentration within the electrochemical gas sensor over the period of time, and, based on data in a look-up table stored in memory 504 that correlates a rate of change of electrolyte concentration to a relative humidity value, determining the relative humidity value corresponding to the average rate of change of electrolyte concentration—at an average ambient temperature determined by the temperature measurement circuitry 501 and an average electrolyte water vapor pressure determined by the pressure measurement circuitry 503—over the period of time. The humidity measurement circuitry 510 may be configured to correlate the determined relative humidity value from the look-up table to the average ambient humidity over the period of time. In various embodiments, the humidity measurement circuitry 501 may be configured to communicate with one or more of the various components of the controller 500.

The user interface circuitry as described herein may include hardware components designed or configured to receive, process, generate, and transmit data, such as user interface data. In some embodiments, the user interface circuitry may be configured to generate user interface data indicative of a set of monitoring modes for a particular gas type or environment, electrochemical gas monitoring signals, RMS electrochemical gas monitoring signals, predetermined electrochemical gas monitoring threshold value (e.g., settable by a user using input-output circuitry 504 or a user device in communication with input-output circuitry 504; settable by accessing a table of predetermined electrochemical gas monitoring threshold values for various gas types), electrochemical gas alert signals, electrolyte content monitoring signals, RMS electrolyte content monitoring signals, electrolyte content values (including, but not limited to, electrolyte content percentage values), low electrolyte alert signals, pressure values, ambient temperature values, ambient humidity values, and combinations thereof. In some instances, the user interface data may comprise a list (e.g., a selectable drop-down list, a ordered grouping of selectable icons (e.g., clickable icons configured to be clicked by a mouse; virtual icons configured to be displayed on a touchscreen and pressed by a user's finger), a text-based prompt, a voice-based prompt) of monitoring modes. For instance, the user interface circuitry may include hardware components designed or configured to generate the user interface data based on any embodiment or combination of embodiments described with reference to the figures included herein.

In some embodiments, the user interface circuitry may be in communication with a display device (e.g., input-output circuitry 504, a user device, or a display device communicatively coupled thereto) and thus configured to transmit the user interface data to the display device. For example, the user interface circuitry may be configured to generate user interface data and transmit the generated user interface data to the input-output circuitry 504, and the input-output circuitry 504 may be configured to receive the user interface data and display the received user interface data on one or more display screens.

In some embodiments, each of the electrochemical gas monitoring circuitry 511, electrochemical gas detection circuitry 512, electrolyte content monitoring circuitry 509, user interface circuitry, temperature measurement circuitry 501, pressure measurement circuitry 503, and humidity measurement circuitry 510 may include a separate processor, specially configured field programmable gate array (FPGA), application specific interface circuit (ASIC), or cloud utility to perform the above functions. In some embodiments, the hardware components described above with reference to the electrochemical gas monitoring circuitry 511, electrochemical gas detection circuitry 512, electrolyte content monitoring circuitry 509, user interface circuitry, temperature measurement circuitry 501, pressure measurement circuitry 503, and humidity measurement circuitry 510 may, for instance, utilize communications circuitry 507 or any suitable wired or wireless communications path to communicate with a user device, each other, or any other suitable circuitry or device.

In some embodiments, one or more of the electrochemical gas monitoring circuitry 511, electrochemical gas detection circuitry 512, electrolyte content monitoring circuitry 509, user interface circuitry, temperature measurement circuitry 501, pressure measurement circuitry 503, and humidity measurement circuitry 510 may be hosted locally by the controller 500. In some embodiments, one or more of the user interface circuitry and the humidity measurement circuitry 510 may be hosted remotely (e.g., by one or more cloud servers) and thus need not physically reside on the controller 500. Thus, some or all of the functionality described herein may be provided by a remote circuitry. For example, the controller 500 may access one or more remote circuitries via any sort of networked connection that facilitates transmission of data and electronic information between the controller 500 and the remote circuitries. In turn, the controller 500 may be in remote communication with one or more of the electrochemical gas monitoring circuitry 511, electrochemical gas detection circuitry 512, electrolyte content monitoring circuitry 509, user interface circuitry, temperature measurement circuitry 501, pressure measurement circuitry 503, and humidity measurement circuitry 510.

As described above and as will be appreciated based on this disclosure, embodiments of the present disclosure may be configured as systems, apparatuses, methods, mobile devices, backend network devices, computer program products, other suitable devices, and combinations thereof. Accordingly, embodiments may comprise various means including entirely of hardware or any combination of software with hardware. Furthermore, embodiments may take the form of a computer program product on at least one non-transitory computer-readable storage medium having computer-readable program instructions (e.g., computer software) embodied in the storage medium. Any suitable computer-readable storage medium may be utilized including non-transitory hard disks, CD-ROMs, flash memory, optical storage devices, or magnetic storage devices. As will be appreciated, any computer program instructions and/or other type of code described herein may be loaded onto a computer, processor or other programmable apparatus's circuitry to produce a machine, such that the computer, processor, or other programmable circuitry that executes the code on the machine creates the means for implementing various functions, including those described herein.

In some embodiments, the user device may be embodied by one or more computing devices or systems that also may include processing circuitry, memory, input-output circuitry, and communications circuitry. For example, a user device may be a laptop computer on which an app (e.g., a GUI application) is running or otherwise being executed by processing circuitry. In yet another example, a user device may be a smartphone on which an app (e.g., a webpage browsing app) is running or otherwise being executed by processing circuitry. As it relates to operations described in the present disclosure, the functioning of these devices may utilize components similar to the similarly named components described above with respect to FIG. 5. Additional description of the mechanics of these components is omitted for the sake of brevity. These device elements, operating together, provide the respective computing systems with the functionality necessary to facilitate the communication of data with the example electrochemical gas sensor described herein.

As described above and as will be appreciated based on this disclosure, various embodiments may be configured in various forms including with portions of the gas detection apparatus 100 being remote from gas detection apparatus 100 shown in FIG. 6. FIG. 6 illustrates exemplary data flows among various components in accordance with a gas detection apparatus 100 embodiment as discussed herein. In various embodiments, the communication circuitry 507 may be configured so as to enable wireless communication from the gas detection apparatus 100 within an Internet-of-Things (IoT) network 600 to a variety of wirelessly enabled devices (e.g., a user mobile device 601, a server 602, a computer 603, a second gas detection apparatus 604). In an exemplary embodiment, the gas detection apparatus 100 may be configured to communicate any of the aforementioned sensory results or readings communicated to the processing circuitry 508 (e.g., electrochemical gas monitoring circuitry 511 output, temperature measurement circuitry 501 output, pressure measurement circuitry 503 output, humidity measurement circuitry 510 results) to a second gas detection apparatus 604 configured for wireless communication and present within substantially the same ambient environment. In various embodiments, the second gas detection apparatus 604 may comprise one or more gas detection apparatuses as disclosed herein. In various embodiments, the second gas apparatuses 604 may comprise an electrolyte-based electrochemical gas sensor for which the electrolyte concentration may not be easily ascertained. For example, the second gas detection apparatus 604 may comprise an electrolyte-based electrochemical gas sensor utilizing a non-acid-based electrolyte, such as a salt-based electrolyte, an ionic liquid-type electrolyte, or an organic electrolyte. In various embodiments, the gas detection apparatus 100 may communicate an average humidity value within an ambient environment as determined by the humidity measurement circuitry 510 of the gas detection apparatus 100 to the one or more secondary gas detection apparatuses 604. In various embodiments, the one or more secondary gas detection apparatuses 604 may be configured to respectively receive the average humidity value, thus enabling the compensation of the apparatuses' respective sensor outputs.

Method of Use

Figure 7:
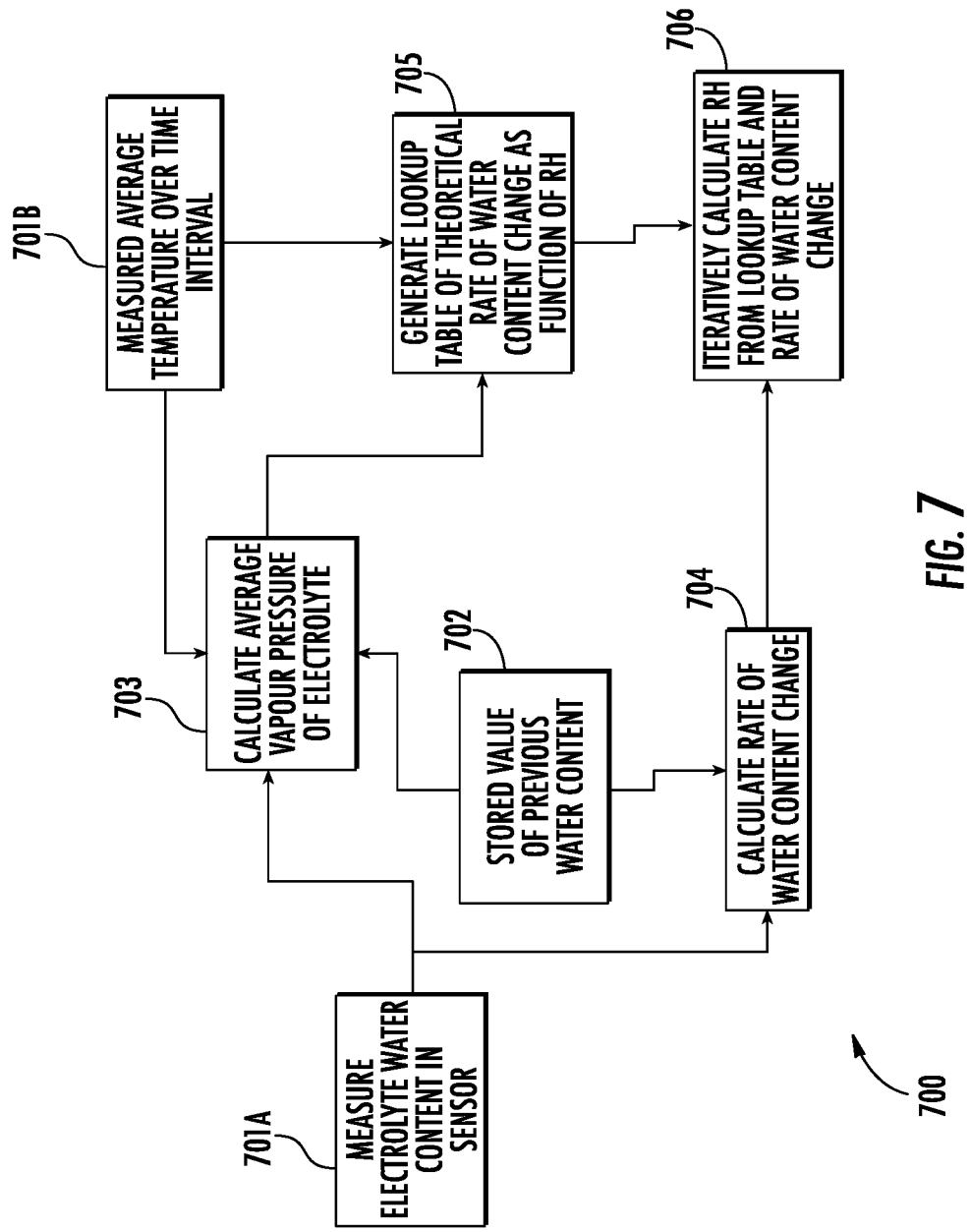
FIG. 7 illustrates a flow diagram of an exemplary method of measuring humidity using an electrochemical gas sensor in accordance with some example embodiments described herein.

FIG. 7 illustrates a block diagram of an exemplary method 700 for measuring humidity using an electrochemical gas sensor.

The method 700 begins with step 701, in which electrolyte concentration and average temperature a first measured. In particular, as shown in step 701A, the electrolyte concentration of an electrochemical gas sensor within a gas detection apparatus is first measured. Methods for measuring the electrolyte concentration of an electrochemical gas sensor as disclosed herein, or any other applicable means for determining electrolyte concentration of an electrochemical gas sensor may be implemented. In various embodiments, the time at which the electrolyte concentration of the electrochemical gas sensor is measured may define the end of a first time interval.

As shown in step 701B, the average temperature of an ambient environment within which the exemplary gas detection apparatus is located is measured over a first period of time. In various embodiments, the average ambient temperature over a first period of time may be measured using either an electrochemical gas sensor or a temperature sensor, and corresponding temperature measurement circuitry (e.g., temperature measurement circuitry 501).

Next, at step 702, a value associated with the electrolyte concentration of the electrochemical gas sensor is stored at the beginning of the first period of time in a memory module (e.g., memory 504). In various embodiments, the stored electrolyte concentration value may comprise a value associated with the electrolyte concentration of the electrochemical gas sensor at the end of a period of time immediately preceding the first period of time.

Next, at step 703, the average electrolyte water vapor pressure of an electrochemical gas sensor over the first period of time is determined. In various embodiments, the electrolyte water vapor pressure may be a function of one or more of the measured electrolyte concentration values of the electrochemical gas sensor and the measured ambient temperature. In various embodiments, the average electrolyte water vapor pressure over a period of time may be a function of the measured electrolyte concentration value measured by the electrochemical gas sensor at the end of the first period of time (i.e. the value measured at step 701A), the stored value associated with the electrolyte concentration of an electrochemical gas sensor at the beginning of the first period of time, and the measured average ambient temperature over the first period of time. In various embodiments, the average electrolyte water vapor pressure in the electrochemical gas sensor over the first time period may be determined using pressure measurement circuitry (e.g., pressure measurement circuitry 503).

Next, at step 704, an average rate of change of electrolyte concentration within an electrochemical gas sensor over the first period of time is determined. In various embodiments, the average rate of change of electrolyte concentration within an electrochemical gas sensor over the first period of time may be determined by dividing the difference between the stored value associated with the electrolyte concentration of an electrochemical gas sensor at the beginning of the first period of time and the electrolyte concentration value measured by the electrochemical gas sensor at the end of the first period of time (i.e. the value measured at step 701A) by the length of the first period of time.

Next, at step 705, one or more look-up tables correlating a rate of change of electrolyte concentration within an electrochemical gas sensor to a corresponding ambient humidity value at various ambient temperature and electrolyte water vapor pressure values are generated and stored within in a memory module (e.g., memory 504). In various embodiments, each look-up table may define the relationship between a rate of change of electrolyte concentration within an electrochemical gas sensor to a corresponding humidity value for a given ambient temperature/electrolyte water vapor pressure combination.

Next, at step 706, a stored look-up table to determine the average humidity value of the ambient environment over the first period of time based on the average rate of change of electrolyte concentration within the electrochemical gas sensor over the first period of time is used. In various embodiments, the appropriate look-up table configuration may be generated and/or determined based on the measured average ambient temperature and average electrolyte water vapor pressure over the first time period. In various embodiments, the generated look-up table may indicate that the measured average rate of change of electrolyte concentration within the electrochemical gas sensor over the first period of time may correspond to a specific ambient humidity value. In various embodiments, that specific corresponding ambient humidity value may be determined to be the average humidity value of the ambient environment over the first period of time.

Figure 8:
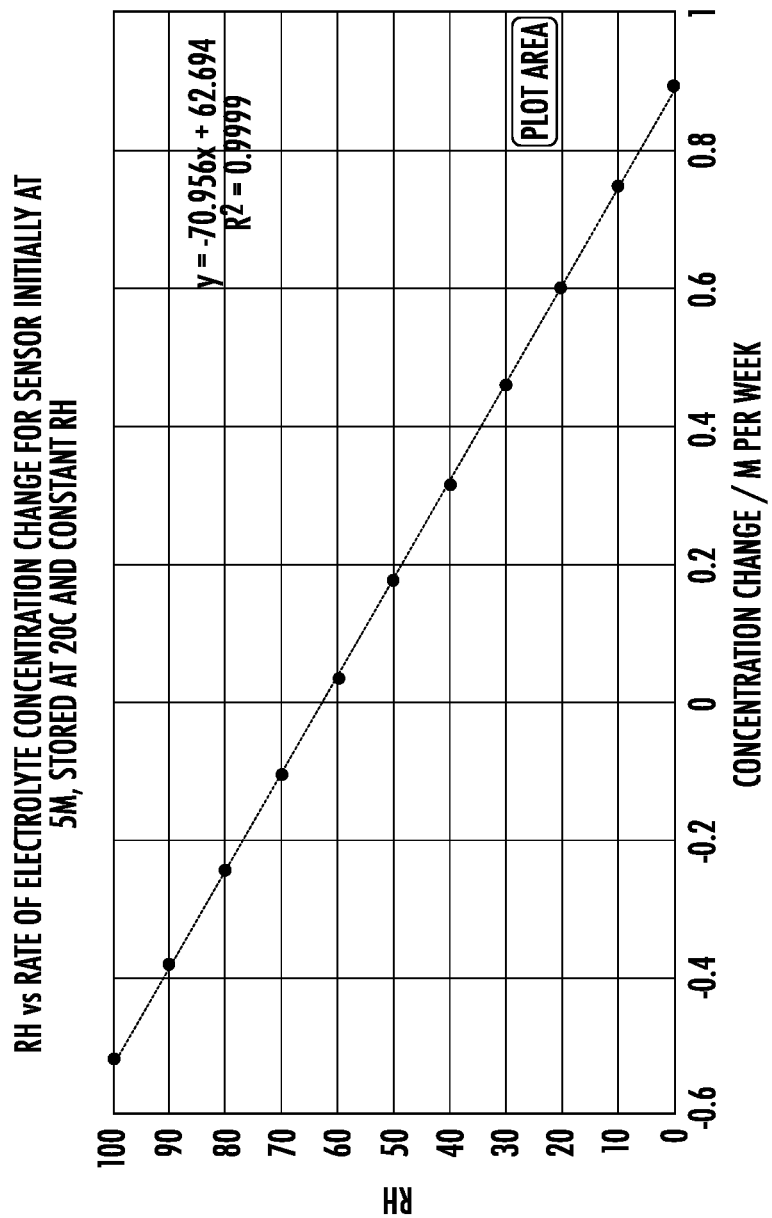
FIG. 8 illustrates an exemplary graphical representation of data produced by a testing configuration in accordance with various embodiments.
Figure 9:
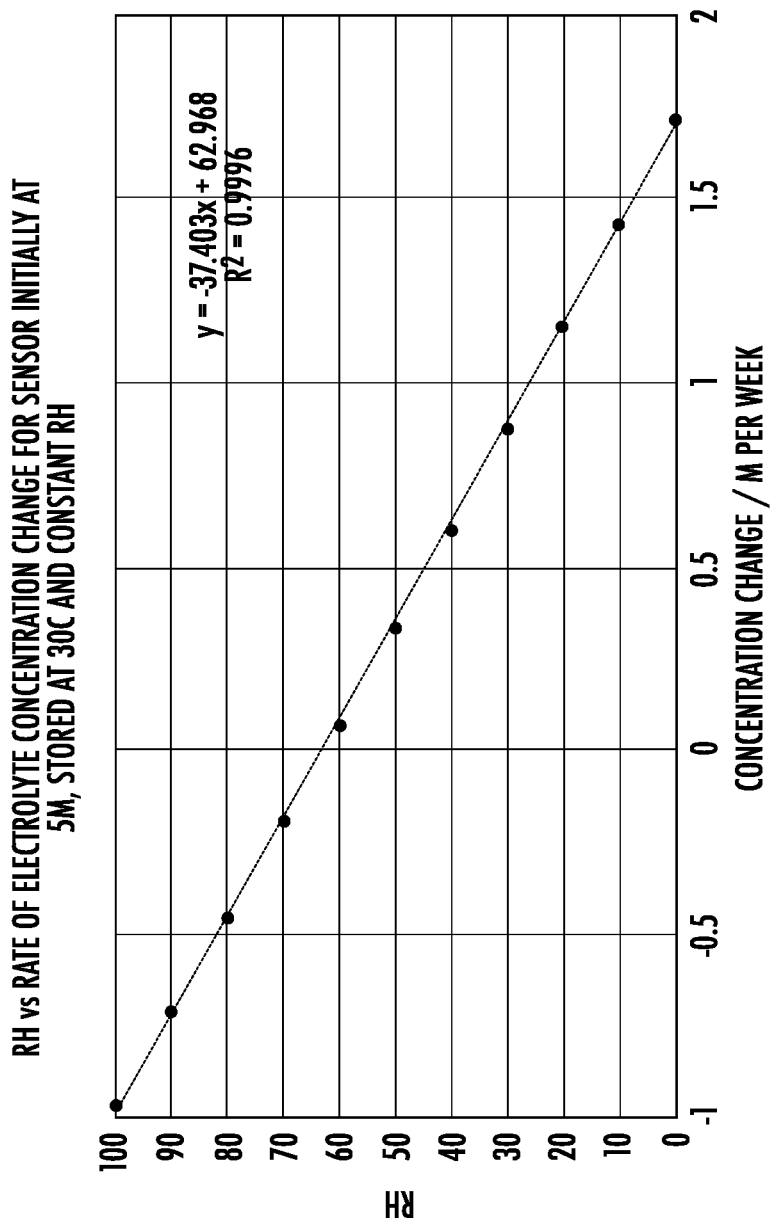
FIG. 9 illustrates an exemplary graphical representation of data produced by a testing configuration in accordance with various embodiments.
Figure 10:
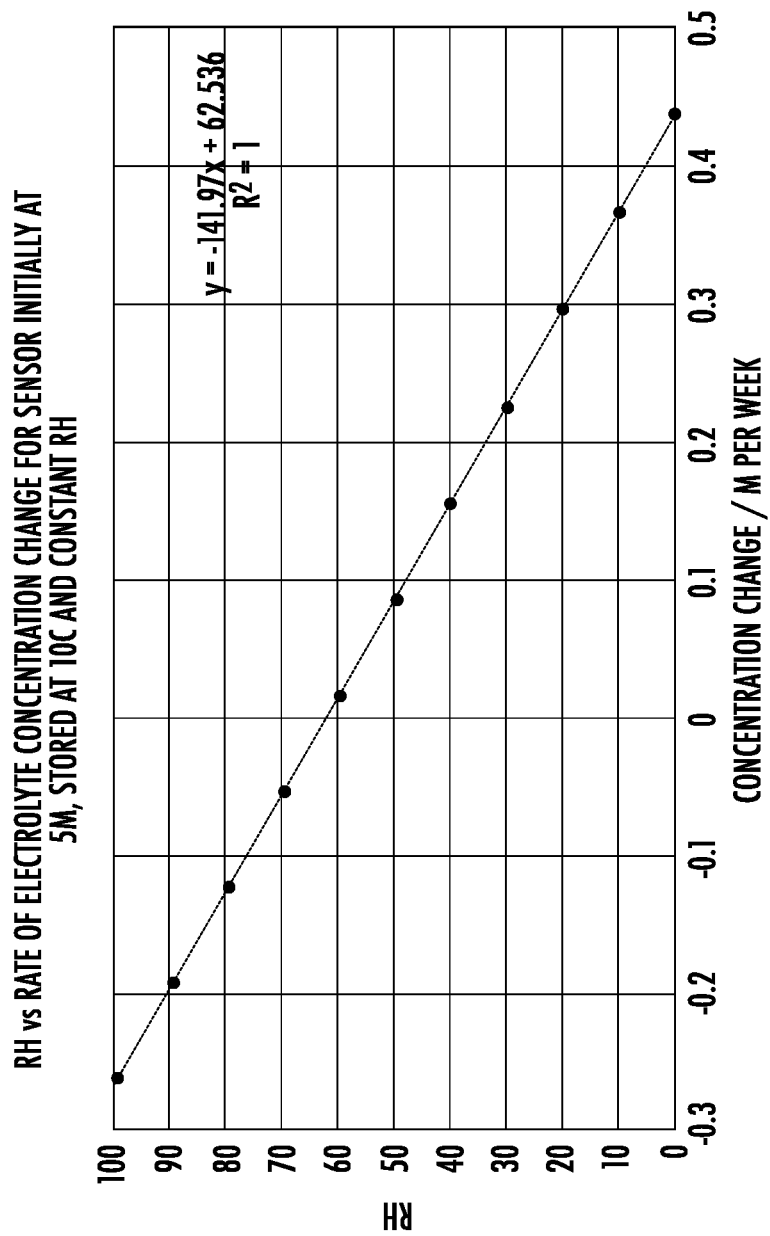
FIG. 10 illustrates an exemplary graphical representation of data produced by a testing configuration in accordance with various embodiments.

FIGS. 8-10 each show graphical representations of the data collected in various experimental trials of embodiments of the claimed invention. FIGS. 8-10 each graphically illustrate the relationship between relative humidity and the rate of change of electrolyte concentration within an exemplary electrolyte gas sensor. As shown in FIGS. 8-10, the relative humidity may is measured along the y-axis and the rate of change of electrolyte concentration is measured along the x-axis. In various embodiments, FIGS. 8-10 may graphically illustrate data defined by one or more exemplary look-up tables as described herein.

The data represented by FIG. 8 represents the behavior of a volume of acid-based electrolytes in an electrolyte-based electrochemical gas sensor over a period of time at a constant 20 degrees Celsius. The initial electrolyte concentration was 5 M at the beginning of the period of time. The illustrated relationship is defined by the equation y=−70.956x+62.694, with an $R^2$ value of 0.9999.

The data represented by FIG. 9 represents the behavior of a volume of acid-based electrolytes in an electrolyte-based electrochemical gas sensor over a period of time at a constant 20 degrees Celsius. The initial electrolyte concentration was 5 M at the beginning of the period of time. The illustrated relationship is defined by the equation y=−37.403x+62.968, with an $R^2$ value of 0.9996.

The data represented by FIG. 10 represents the behavior of a volume of acid-based electrolytes in an electrolyte-based electrochemical gas sensor over a period of time at a constant 10 degrees Celsius. The initial electrolyte concentration was 5 M at the beginning of the period of time. The illustrated relationship is defined by the equation y=−141.97x+62.536, with an $R^2$ value of 1.

As can be understood from the figures and descriptions presented above, the accuracy of the method for determining the average humidity value in an ambient environment by an electrochemical gas sensor may vary proportionally with the ambient temperature. That is, as the temperature increases, the accuracy of the determined average humidity improves; as the temperature decreases, the accuracy of the determined average humidity worsens. For example, using an embodiment of the method as described herein, in an ambient environment that is 20 degrees Celsius, the average humidity value over a one-week time period may be measured to an accuracy of within 7%. Further, in an ambient environment that is 30 degrees Celsius, the average humidity value over a one-week time period may be measured to an accuracy of within 14%. Similarly it may be understood that the increasing the length of the time period over which the measurements described above are taken is understood to improve the accuracy of the measured average humidity in proportion. In various embodiments, the an exemplary time interval for measurement may comprise between five minutes and one month (e.g., one week).

CONCLUSION

Many modifications and other embodiments will come to mind to one skilled in the art to which this disclosure pertains having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A gas detection apparatus comprising:
a first electrolyte-based electrochemical gas sensor configured to measure an electrolyte concentration within the first electrochemical gas sensor;
a temperature sensor configured to measure a temperature of an ambient environment surrounding the first electrolyte-based electrochemical gas sensor; and
a controller configured to determine an average humidity value of the ambient environment based on an average ambient temperature and an average rate of change of electrolyte concentration measured over a period of time.

2. The apparatus of claim 1, wherein the first electrochemical gas sensor comprises a volume of acid-based electrolyte.

3. The apparatus of claim 1, wherein the controller is further configured to determine an average electrolyte water vapor pressure over a period of time.

4. The apparatus of claim 1, further comprising a gas detection apparatus housing, wherein the gas detection apparatus housing comprises an exterior housing portion and an interior housing portion, and wherein the first electrochemical gas sensor, the temperature sensor, and the controller are enclosed within the interior housing portion.

5. The apparatus of claim 1, wherein the average humidity value of the ambient environment over the first period of time is determined using a look-up table correlating the average rate of change of electrolyte concentration within the first electrochemical gas sensor over the first period of time to a corresponding humidity value at the average ambient temperature and an average electrolyte water vapor pressure within the first electrochemical gas sensor over the first period of time, wherein the corresponding humidity value defines the average humidity value of an ambient environment over the first period of time.

6. The apparatus of claim 1, further comprising a second electrochemical gas sensor, wherein the second electrochemical gas sensor is an electrolyte-based electrochemical gas sensor positioned within the ambient environment, and wherein the first electrochemical gas sensor is configured to communicate the average humidity value of the ambient environment over the first period of time to the second electrochemical gas sensor.

7. The apparatus of claim 6, wherein the second electrochemical gas sensor comprises a volume of non-acid-based electrolyte.

8. The apparatus of claim 6, wherein the second electrochemical gas sensor is configured to apply an appropriate compensation factor to an output of the second electrochemical gas sensor based on the average humidity value of the ambient environment over the first period of time.

9. The apparatus of claim 1, further comprising a communication module for communicating calculated average humidity value to other devices in an IoT network for displaying and/or processing the received values.

10. A method of determining ambient humidity comprising:
measuring electrolyte concentration in a first electrolyte-based electrochemical gas sensor over a first period of time;
measuring temperature of ambient environment surrounding first electrolyte-based electrochemical gas sensor using a temperature sensor over the first period of time;
determining, using a controller, an average humidity value of the ambient environment over the first period of time based on an average ambient temperature and an average rate of change of the electrolyte concentration measured over the period of time.

11. The method of claim 10, wherein the first electrochemical gas sensor comprises a volume of acid-based electrolyte.

12. The method of claim 10, wherein the controller is further configured to determine an average electrolyte water vapor pressure over a period of time.

13. The method of claim 10, wherein the temperature sensor is integrated into the first electrochemical gas sensor.

14. The method of claim 13, further comprising providing a gas detection apparatus housing, wherein the gas detection apparatus housing comprises an exterior housing portion and an interior housing portion, and wherein the first electrochemical gas sensor, the temperature sensor, and the controller are enclosed within the interior housing portion.

15. The method of claim 10, wherein the average humidity value of the ambient environment over the first period of time is determined using a look-up table correlating the average rate of change of electrolyte concentration within the first electrochemical gas sensor over the first period of time to a corresponding humidity value at the average ambient temperature and an average electrolyte water vapor pressure within the first electrochemical gas sensor over the first period of time, wherein the corresponding humidity value defines the average humidity value of an ambient environment over the first period of time.

16. The method of claim 10, further comprising providing a second electrochemical gas sensor and communicating the average humidity value of the ambient environment over the first period of time from the first electrochemical gas sensor to the second electrochemical gas sensor, wherein the second electrochemical gas sensor is an electrolyte-based electrochemical gas sensor positioned within the ambient environment.

17. The method of claim 16, wherein the second electrochemical gas sensor comprises a volume of non-acid-based electrolyte.

* * * * *